(12) United States Patent
Stockfisch

(10) Patent No.: US 7,269,597 B2
(45) Date of Patent: Sep. 11, 2007

(54) CHART-AHEAD METHOD FOR DECISION TREE CONSTRUCTION

(75) Inventor: Thomas P. Stockfisch, Escondido, CA (US)

(73) Assignee: Accelrys Software, Inc., San Diego, CA (US)

(*) Notice: Subject to any disclaimer, the term of this patent is extended or adjusted under 35 U.S.C. 154(b) by 431 days.

(21) Appl. No.: 10/737,722

(22) Filed: Dec. 15, 2003

(65) Prior Publication Data

US 2004/0181553 A1 Sep. 16, 2004

Related U.S. Application Data

(60) Provisional application No. 60/434,169, filed on Dec. 16, 2002.

(51) Int. Cl.
G06F 17/00 (2006.01)
G06F 7/00 (2006.01)
(52) U.S. Cl. ............... 707/102; 707/101; 707/104.1; 707/7
(58) Field of Classification Search ........... 707/102, 707/101, 7, 104.1; 706/45; 725/116
See application file for complete search history.

(56) References Cited

U.S. PATENT DOCUMENTS

| 6,029,195 | A * | 2/2000 | Herz | 725/116 |
| 6,735,596 | B2 * | 5/2004 | Corynen | 707/102 |
| 6,750,864 | B1 * | 6/2004 | Anwar | 345/440 |
| 6,868,423 | B2 * | 3/2005 | Ohta et al. | 707/102 |
| 6,941,318 | B1 * | 9/2005 | Tamayo et al. | 707/102 |
| 7,016,887 | B2 * | 3/2006 | Stockfisch | 706/45 |
| 2002/0087499 | A1 | 7/2002 | Stockfisch | |

OTHER PUBLICATIONS

Construction of Tree Structured Classifiers by the MDL Principle, Marti Wax, CH2847-3/90/0000-2157, 1990 IEEE.*
Breiman et al., "Classification and Regression Trees," Chapman and Hall/CRC 1984, entire book.
Chatfield et al., "Introduction to Multivariate Analysis," Chapman and Hall (London 1980), Chapter 11, pp. 212-230.
Everitt et al., "Applied Multivariate Data Analysis," Halsted Press (New York 1991), Chapter 6, pp. 99-126.
Everitt, "Cluster Analysis Third Edition," Halsted press (New Yrok 1993), entire book.

* cited by examiner

Primary Examiner—John Cottingham
Assistant Examiner—Kuen S. Lu
(74) Attorney, Agent, or Firm—Knobbe Martens Olson & Bear LLP (57) ABSTRACT

Systems and methods are described for forming a decision tree by considering multiple possible alternative tests or thresholds as well as the possible alternative branches from each test or threshold. This method of making decision trees may be referred to as "look-ahead" or "chart-ahead" recursive partitioning because tests or thresholds can be selected not only for their own ability to divide items into different classes, but also for the ability of future tests or thresholds, enabled by the present tests or thresholds, to further divide items into classes. In preferred embodiments, the method of making the decision tree includes generating clusters of items having similar descriptors and properties, and then evaluating various tests or thresholds for their ability to isolate clusters. Also disclosed are methods of using such decision trees, particularly for the purpose of predicting the unknown properties of molecules.

6 Claims, 5 Drawing Sheets

CHART-AHEAD METHOD FOR DECISION TREE CONSTRUCTION

RELATED APPLICATIONS

This application claims priority to provisional application No. 60/434,169, filed on Dec. 16, 2002, which is hereby incorporated by reference.

BACKGROUND OF THE INVENTION

1. Field of the Invention

This invention relates to methods and systems of predicting properties of molecules.

2. Description of the Related Art

A physical item's unknown conditions can often be predicted based on the item's known conditions. Disease diagnosis is one simple example. If a patient has symptom A, and has symptom B, but does not have symptom C, then it may be predicted that the patient has some particular disease. In this example, the physical item's (the patient's) three known conditions (have symptom A, have symptom B, not have symptom C) are used to predict an unknown condition (that the patient has some particular disease). The conditions that are known or easy to measure or calculate are often called descriptors or X variables. The conditions that are unknown or difficult to measure or calculate, and that are believed to be related to the descriptors, are often called properties, attributes, or Y variables.

Decision trees are a common method of forming predictions about a property of an item, based on descriptors of the item. The structure of a decision tree can be derived by studying existing items. Each of the existing items have known descriptor values and a known property value. The existing items that are used to formulate the decision tree are called training items. The items that have an unknown property and are not used in formulating the decision tree are called new items. The known descriptor values of the training items, in conjunction with the known property values of the training items, are used to develop a connected series of decision points in the form of the decision tree. The decision tree can then be used to predict the unknown property of a new item. For example, based on the descriptors (e.g., age and blood pressure) and the property (whether patient suffered a heart attack) of the training items (medical history data of prior patients), a decision tree can be formulated and then used to predict whether a new patient with given descriptors is likely to suffer a heart attack.

Decision trees classify training items by repeated classification of the training items into classes at nodes of the tree. Classification at each node is based on a test on one or more descriptors (e.g., whether the patient is more than fifty years old, whether blood pressure is greater than 100). Each terminal node (i.e., leaf) of the tree corresponds to a classification of the property. The property of a new item is then predicted by running the new item from the root of the tree through the tests of the decision tree, based on the descriptors of the new item, until a leaf is reached. The property corresponding to the leaf is the predicted property of the new data. In addition to predicting a new property, the decision tree can also aid a user in interpreting relationships between descriptors and the property. For a more detailed description of decision tree methods, please refer to pp. 18-36 of the text of "Classification and Regression Trees", Breiman, Friedman, Olshen and Stone, Chapman & Hall/CRC 1984 (CART hereinafter). For a description of some of the advantages of a tree-structured approach, please refer to pp. 55-58, CART.

The disclosure of the above-described book "Classification and Regression Trees" is hereby incorporated by reference in its entirety.

Decision trees may include both classification trees and regression trees. A classification tree's terminal nodes each represent a class of properties. A regression tree's terminal nodes each represent a value of a property. As those ordinarily skilled in the art will appreciate, the disclosed methods and systems can be applied to both classification trees and regression trees. Therefore, the terms such as "class", "classify" and "classification," can be used in the present application to refer to assigning a class to a classification tree terminal node as well as assigning a value to a regression tree terminal node. The term "decision tree" as used in the application refers to both classification trees and regression trees.

Decision trees and various methods for their construction are further disclosed in U.S. Pat. No. 7,016,887, issued on Mar. 21, 2006, hereby expressly incorporated by reference in its entirety.

There exists an unmet need in the art for a method of quickly generating improved decision trees which have higher accuracy in predicting the properties of various molecules while simultaneously having a smaller number of leaves. Smaller trees tend to be more predictive on molecules outside the training set, and are also easier to interpret.

SUMMARY OF THE INVENTION

One aspect of the present invention is a method of forming a decision tree that includes a hierarchical set of nodes and that predicts properties of interest of physical items by testing characteristics of physical items against defined thresholds at each of a series of nodes of the hierarchy, wherein the physical items have two or more known characteristics and at least one unknown property of interest and the method includes defining tests or thresholds for a series of two or more nodes in the hierarchy by determining the total combined predictive accuracy of the series of nodes under a plurality of alternative test or threshold definitions for at least one of the nodes in the series.

Another aspect of the present invention is a method of forming a decision tree, wherein the decision tree operates to provide predictions of at least one attribute of interest of a physical item, wherein the physical item has one or more measured or computed descriptors representative of one or more physical characteristics of the physical item, and wherein the physical item has one or more unknown attributes of interest which have not been physically measured or otherwise previously determined, and wherein the decision tree includes two or more nodes in a hierarchical structure, wherein each node is defined by a test based on one or more of the physical items' descriptors, and wherein the result of the test at a node operates to classify the physical item into one of two or more classes, and wherein the classification made at any given node determines the identity of a node lower in the hierarchy which is next applied to the physical item until a final node in the hierarchy is reached, and wherein the classification made by the final node includes a prediction of the behavior of the physical item with respect to the unknown attribute of interest, and wherein the method of forming the decision tree includes the steps of: providing a set of training physical items, each training physical item in the set of training physical items having one or more measured or computed physical descriptors and one or more attributes of interest which have been physically measured or previously determined; defining a set of two or more alternative tests for defining a selected node of the decision tree; defining at least one test for defining at least one node lower in the hierarchy for each of the alternative tests previously defined for the selected node higher in the hierarchy; determining the results of applying at least the selected node and the at least one node lower in the hierarchy to the set of training physical items; and choosing one of the alternative tests from the set to define the selected node based on the determined results.

Another aspect of the present invention is a method of forming a decision super tree, the decision super tree operating to provide a plurality of predictions of at least one property of interest of a physical item, wherein the physical item has one or more measured or computed descriptors representative of one or more physical characteristics of the physical item and one or more physical properties of interest, and wherein the super tree comprises a plurality of nodes in a hierarchical structure, the plurality of nodes defined by at least one test based on at least one of the one or more physical characteristics, at least one of the plurality of nodes comprising a plurality of alternative tests such that each alternative test results in an alternative prediction of the at least one property of interest, the method including the steps of: providing a set of training physical items, the set of items having one or more physical descriptors and one or more physical properties of interest; creating a first node that includes two or more alternative tests based on one or more of the set of items' physical descriptors, wherein each test operates to classify training items into two or more classes; and creating one or more additional nodes that includes two or more alternative tests based on one or more of the set of items' physical descriptors, wherein each additional node operates on one of the two or more classes created by the first node and each alternative test in each additional node test operates to further classify the training items into two or more classes for each additional node.

Still another aspect of the present invention is a method of pruning a decision super tree including discarding all but one alternative test at each node to produce one or more decision trees.

Another aspect of the present invention is a method of clustering a set of items, the set of items having a plurality of numeric physical descriptors and one or more physical properties, at least one of the properties being characterized by a non-numeric value, wherein the method includes the steps of: for each item, representing each property that has a non-numeric value with a numeric value and using a clustering algorithm to cluster the items into subsets of items that have similar descriptor values, similar values among numeric values that represent non-numeric property values, and similar values for properties inherently characterized by a numerical value, if any.

Another aspect of the present invention is a method of forming a decision tree, the decision tree operating to provide predictions of the behavior of a physical item with respect to at least one attribute of interest, wherein the physical item has one or more measured or computed descriptors representative of one or more characteristics of the physical item, and wherein the physical item exhibits unknown behavior with respect to at least one attribute of interest, and wherein the decision tree includes two or more nodes in a hierarchical structure, wherein each node is defined by a test based on one or more of the physical items' descriptors, wherein the result of the test at a given node operates to categorize the physical item into one of a plurality of categories, and wherein the categorization made at any given node determines the identity of a node lower in the hierarchy which is next applied to the physical item until an end node of the hierarchy is reached, and wherein the classification made by the end node comprises a prediction of the behavior of the physical item with respect to the unknown attribute of interest, wherein the method of forming the decision tree includes the steps of: providing a set of training physical items, each training physical item in the set of training physical items having one or more measured or computed physical descriptors and one or more attributes of interest which have been physically measured or previously determined; clustering the training items into a plurality of clusters defined by similarity in both descriptors and attributes; and defining at least one of the nodes during tree formation based on an improvement in cluster purity when the training items are partitioned at the node irrespective of improvement or degradation of class purity when the training items are partitioned at the node.

Another aspect of the present invention is a computer implemented system for constructing decision trees for predicting the behavior of a physical item with respect to an attribute of interest, the system including: a memory storing a set of measured or computed characteristics for each of a set of training physical items, the memory also storing information assigning each of the training physical items with a behavioral classification defining an aspect of each training item's actual physical behavior with respect to an attribute of interest; a clustering module operative to assign each of the training physical items to one of a plurality of clusters of training items, the clusters defined by similarities in characteristics and in behavioral classification among subsets of the set of training physical items; a test definition module operative to define tests and test thresholds for separating the training physical items into separate groups when the test and test thresholds are applied to the characteristics; and a decision tree construction module operative to store a hierarchical set of nodes, each node defined by a test and test threshold created by the test definition module; wherein the test definition module and decision tree construction module create and store several alternative node definitions during tree construction, wherein one of the alternative node definitions produces maximum association between the groups and the clusters, and wherein another of the alternative node definitions produces maximum association between the groups and the behavioral classifications.

DETAILED DESCRIPTION OF THE PREFERRED EMBODIMENT

In the present disclosure, the following terms are to be interpreted as having the corresponding definitions:

As used herein, the term "decision tree" means a hierarchical structure for inquiring about an item's known descriptors (X values) in an attempt to predict one or more properties or attributes (Y values) of the item. Typically, a decision tree consists of a single root followed by a hierarchy of nodes. A node is a leaf node if there are no additional nodes beyond it. Alternatively, a node can operate to split into two or more branches. These branches in turn contain one or more additional nodes. Nodes that split into two or more branches are defined by tests or thresholds based on one or more of the item's known descriptors (X values). The result of the tests or thresholds at each node operates to classify the item into one of two or more classes. Nodes lower in the hierarchy are applied to the item until a leaf node is reached. Classification that results in a leaf node provides a prediction of the one or more properties of the item. In one embodiment of the present invention, a decision tree is constructed by evaluating all possible classifications at each node in terms of the improvement in prediction provided by the nodes immediately lower in the hierarchy. In another embodiment, improvement in prediction is considered after the application of two or more nodes in series lower in the hierarchy.

As used herein, the term "conventional recursive partitioning" means generating a decision tree by selecting a test or threshold for each non-leaf node over other possible tests or thresholds because the test or threshold best improves the purity of the resulting classes based on items' properties (Y values) or otherwise minimizes some objective function of only the current node.

As used herein, the term "chart-ahead recursive partitioning" means recursive partitioning which designates a test or threshold at a particular node after considering the result of one or more tests or thresholds at subsequent nodes that would be enabled by the present test or threshold.

As used herein, the term "cluster" means a subset of items which have similar X values as well as similar Y values which are not shared with all the items of the complete set. Various clustering methods are available and are discussed infra.

As used herein, the term "super tree" means a tree that can have more than one alternative test or threshold at each node. It is an efficient representation of all decision trees that can be produced by eliminating all but at most one alternative test or threshold at each node.

As used herein, the term "pruning" means removing one or more branches of a decision tree; more specifically, pruning a branch means deleting from the tree all descendents of the branch, i.e., cutting off all nodes of the branch except the root node of the branch. A sub-tree is the original tree minus the pruned branch. Pruning a super tree generally involves creating a single tree by removing all but one of the alternative tests or thresholds at each node. Pruning a super tree may also include the deletion of one or more branches, though such deletion is not always necessary.

As used herein, the term "descriptors" means measured or computed values that are representative of physical characteristic of physical items.

As used herein, the terms "property of interest" and "attribute of interest" means a physical behavior of a physical item that is of interest. The behavior may be represented by a numeric value or a non-numeric classification. In some embodiments, the behavior is measured or in some other way determined so that the item can be used as a training item. In other embodiments, the behavior is not measured but is predicted by a decision tree.

In conventional recursive partitioning tree growth, a set of training items is provided with known descriptors and known one or more properties. Tests or thresholds are chosen for each node based on how well the tests or thresholds classify the set of training items based on the known one or more properties. For example, for items containing two numeric descriptors and one attribute characterizing whether or not the items have a specified property, the root node may be defined such that it divides the set of training items into two classes based on whether the first descriptor value is above or below some threshold value. The threshold value is determined based on the value that will most accurately divide the set of training items into one class of items having the specified property and one class of items not having the specified property. Thus, the threshold value is chosen to maximize the "class purity" of the two classes. Two additional nodes at a lower level in the hierarchy will act on each class of items respectively to further divide the items based on threshold values for the second descriptor value. These additional threshold values will likewise be determined based on the values that will most accurately divide the respective classes into additional classes that are the most pure based on the specified property. Thus, a hierarchical decision tree is created that results in four leaf nodes.

Conventional recursive partitioning looks only at how best to classify a set using a series of single operations wherein those operations are selected on their own merit without any consideration of the effect that classifications in nodes higher up in the hierarchy might have on classifications in nodes lower in the hierarchy. Conventional recursive partitioning, although it creates nodes that work well individually, is not equipped to create nodes that work well together. This is because it does not provide for defining a test or threshold at a given node with the effectiveness of subsequent tests or thresholds in mind (except in a fortuitous way). Further, under conventional recursive partitioning, once a given node is created, that node cannot be revisited, except to delete it permanently during pruning. One embodiment of the present invention is a method of creating a decision tree using a "look-ahead" or "chart-ahead" approach to a recursive partitioning algorithm that addresses the shortcomings of conventional recursive partitioning.

The Chart-Ahead Method Generally

Chart-ahead recursive partitioning represents an improvement over conventional recursive partitioning because it enables the creation of nodes with tests or thresholds which may not themselves create a profound increase in class purity, but nevertheless enable subsequent tests or thresholds that do. Conventional recursive partitioning would reject such a low-yield node as ineffectual and undesirable because it is less a step forward than other nodes would be. Viewed by itself, such a node is not as good as other nodes and mathematically should not be selected. However, chart-ahead partitioning seeks to compare the effectiveness of paths through multiple nodes rather than the effectiveness of individual nodes in a path.

For example, if a recursive partitioning algorithm is intended to predict whether a particular person is living or deceased, knowing that person's gender is not especially helpful on its own; males are not substantially more or less likely to be deceased than females. However, if the first node is based on gender and the second node is based on age, the male side of the tree can use the median life expectancy for males and the female side can use the median life expectancy for females. The result is a four-leaf decision tree that more accurately predicts whether a given person is living or deceased than any four-leaf tree that starts by classifying based on the median life expectancy for all humans and afterwards queries gender. Conventional recursive partitioning would not have discovered this better tree because it would not have considered gender to be a worthwhile starting partition.

Figure 1:
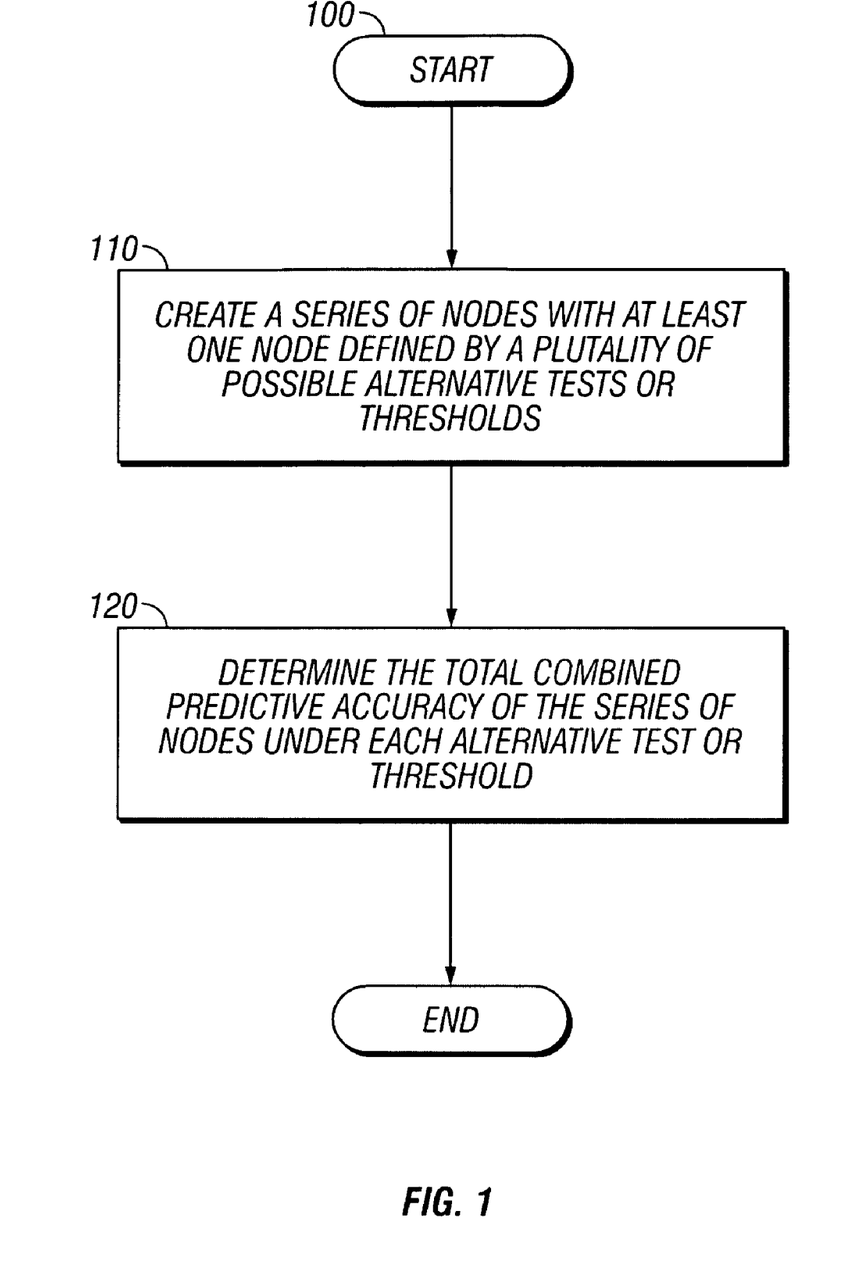
FIG. 1 depicts a flow chart illustrating the creation of a decision tree including defining possible alternative tests for at least one node.

One method of growing a decision tree based on chart-ahead recursive partitioning is illustrated by the flow chart in FIG. 1. The process begins at start block 100. At block 110, a series of nodes are created in a hierarchical structure and defined by tests or thresholds. For at least one of the nodes, a plurality of possible alternative tests or thresholds are defined. At block 120, the total combined predictive accuracy of the series of nodes is determined when using each of the possible alternative tests or thresholds. In this way, choosing among the possible alternative tests or thresholds is based on the accuracy of a series of nodes rather than a single node.

Using a Super Tree

Figure 2:
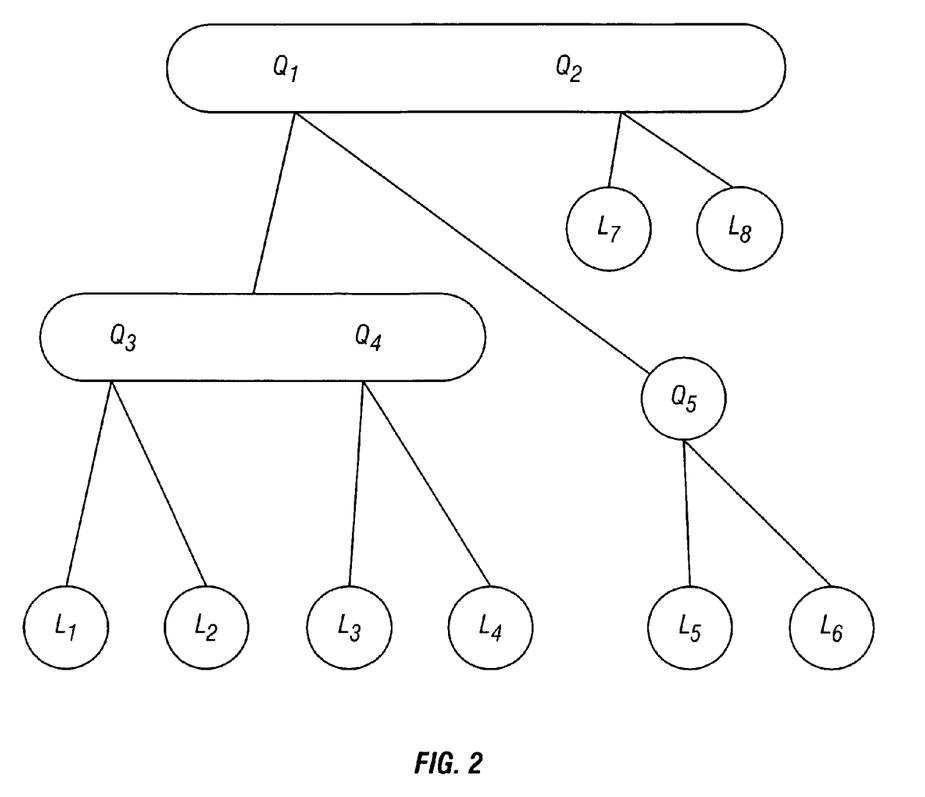
FIG. 2 illustrates one embodiment of a super tree.

In one embodiment, chart-ahead tree growth is implemented using a super tree. One such super tree is illustrated in FIG. 2. As shown in FIG. 2, Q1 and Q2 are possible alternative tests or thresholds for the first node of the tree. Conventional recursive partitioning would choose Q1 or Q2 as the first node's test or threshold based on how well they divide items based on class purity. In a super tree, however, tree construction does not commit to either Q1 or Q2. Rather, branches are created from both Q1 and Q2. Likewise, nodes lower in the hierarchy can have alternative tests or thresholds such as Q3 and Q4. However, not all nodes in a super tree need contain multiple tests or thresholds, as is illustrated in the node containing only the test or threshold Q5. The super tree in FIG. 2 represents multiple possible decision trees. For example, although the super tree contains leaf nodes L1 through L8, the decision trees represented by the super tree include trees with leaf nodes L1, L2, L5, and L6; leaf nodes L3, L4, L5, and L6; and leaf nodes L7 and L8. Such decision trees can be constructed from the super tree by selecting from among the possible alternative tests and thresholds at each node. Use of the super tree in FIG. 2 provides for the consideration of the efficacy of possible second node tests Q3, Q4, and Q5 before committing to either Q1 or Q2 in the first node. Hence, Q2 alone might classify items more effectively than Q1 alone, but if Q1+Q3 partition better than Q2, then the Q1–Q3 path can be selected to create a better decision tree than using the Q2 path.

In various embodiments, any number of possible tests or thresholds may be considered and alternative branches may be considered to any depth. However, depth may have to be limited due to computer memory and speed limitations created by the combinatorial explosion of the size of the super tree as depth is increased. A similar problem is encountered in computer chess playing programs where only a small number of the legal moves at each position can be explored. The maximum depth of the produced tree may be limited as well as the depth to which alternative branches are considered.

Figure 3:
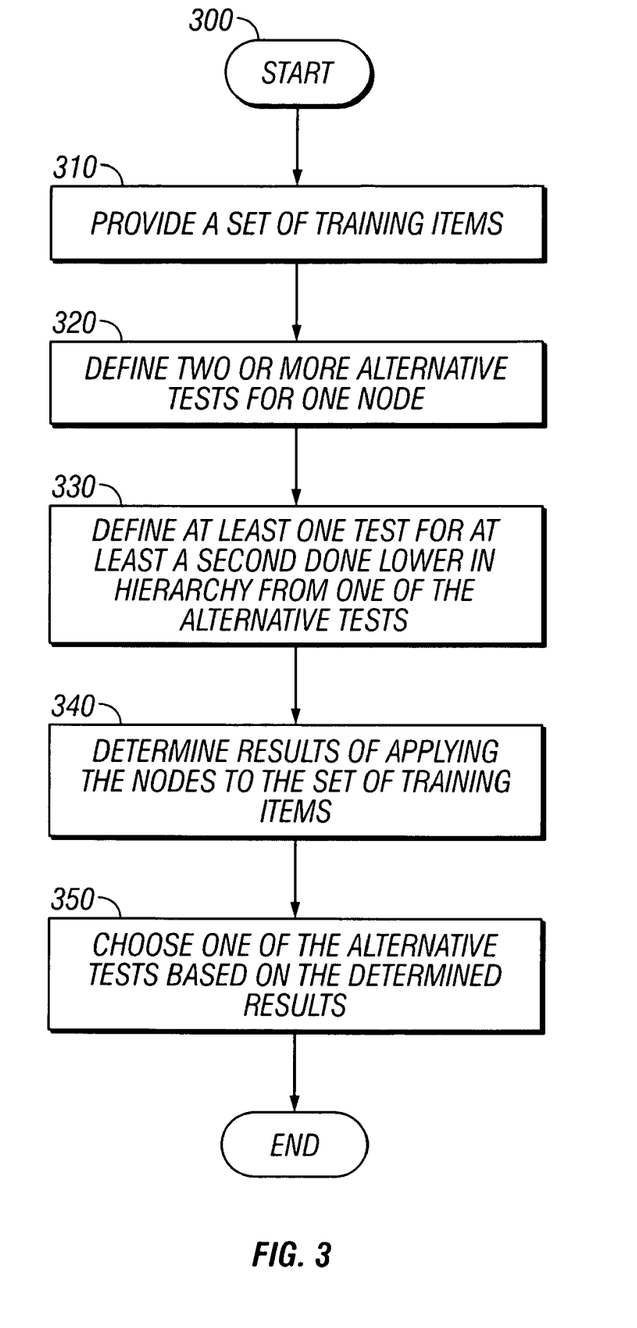
FIG. 3 depicts a flow chart illustrating the creation of a decision tree using a set of training items and defining alternative tests for at least one node.

In one embodiment, depicted by the flowchart in FIG. 3, a decision tree is formed using chart-ahead recursive partitioning using a set of training items. The process starts at start block 300. Next, the set of training items is provided at block 310. The set of training items are physical items that are characterized by one or more measured or computed descriptors representative of one or more physical characteristics of the items. For example, if the set of items is a set of molecules, one descriptor may be the molecular weight of the molecules. The set of training items are also characterized by one or more attributes or properties of interest that have been physically measured or in some other way previously determined. For example, the attribute of a set of molecules may be whether or not the molecules are active for inhibition of a specified enzyme.

At block 320, two or more alternative tests or thresholds are defined for one node of the decision tree. The tests or thresholds operate to classify the set of training items into classes. At block 330, at least one test or threshold is defined for at least a second node lower in hierarchy from one of the alternative tests or thresholds defined at block 320. This test or threshold acts to further classify a class created by one of the tests or thresholds defined in block 320. At block 340, the results of applying at least the two nodes created in block 320 and 330 to the set of training items are determined. The results may indicate how accurately the nodes, and the alternative tests or thresholds defined in block 320, separate the set of training items into classes characterized by the physical attribute of interest (e.g., into a class of molecules having activity and a class of molecules not having activity). At block 350, one of the possible alternative tests or thresholds is chosen based on the results determined at block 340 to define the node created in block 320.

In other embodiments of the present invention, the process depicted in FIG. 3 is modified to include additional nodes. For example, blocks 320 and 330 may be independently repeated to generate additional nodes. Furthermore, if multiple nodes containing alternative tests or thresholds are created, the process at block 350 will involve choosing one alternative test to define each such node.

Generating Alternative Tests or Thresholds

Possible alternative tests or thresholds may be defined by any number of means. In one embodiment, one of the possible alternative tests or thresholds is based on class purity. That is, the test or threshold is defined such that it most accurately classifies items into classes based on the items' one or more properties of interest, as in the tests or thresholds defined in conventional recursive partitioning. Additional possible alternative tests or thresholds may be based on the tests or thresholds that provide the B best class-based scores. For example, the tests that provide the top two class-based scores (B=2) for accuracy of classifying items based on properties of interest may be chosen.

In some embodiments, class-based tests or thresholds may be defined based on improvement in class purity at a given level below the test or threshold. For example, a given test or threshold may be optimized based on the test or threshold that will result in the most accurate classification based on the properties of interest two levels lower in the hierarchy. In such a case, tests or thresholds defined in multiple nodes are optimized simultaneously.

In some embodiments, possible alternative tests or thresholds are defined based on improvement in cluster purity when using a set of training items. In these embodiments, the training items are first clustered into a set of clusters defined by items that have similar descriptors (X values) as well as similar properties (Y values) that are not shared by all of the items. For example, a subset of molecules might comprise a cluster if all the members had a molecular weight in a given range and tended to be pharmaceutically "active" for a particular purpose. For additional information about clustering, see, e.g., Everitt, *Cluster Analysis* 3$^{rd}$ ed., Halsted Press (New York 1993); Everitt et al., *Applied Multivariate Data Analysis*, Halsted Press (New York 1991), at chap. 6; Chatfield et al., *Introduction to Multivariate Analysis*, Chapman and Hall (London 1980), at chap. 11; each of which is hereby incorporated by reference in its entirety.

When using cluster-based tests or thresholds, the tests or thresholds are evaluated for their accuracy in classifying the training items into the clusters in which the items belong. Such a test or threshold may not be very accurate in dividing items based on their properties of interest (class purity); however, they may prove to provide a more accurate prediction of properties of interest at nodes lower in the hierarchy than when using a class-based test. In some embodiments, tests or thresholds having the B' best cluster-based scores may be chosen to generate multiple cluster-based alternative tests or thresholds.

A variety of well known methods can be used to define clusters for the purpose of practicing the invention. One available method is Jarvis-Patrick clustering. However, Jarvis-Patrick clustering can result in too many singletons and the number of clusters produced can become very large and difficult to manage. Preferred clustering methods are the Hierarchical Ward and relocation clustering methods. If there are a large number of descriptors (X values), clustering can be very slow. In this case, first performing a PCA analysis and retaining only the first few components can reduce the number of descriptors. It is preferable to include the items' properties of interest (Y values) in the clustering to be sure that the clusters are relevant to the prediction problem at hand. Other methods that can be used for clustering include, but are not limited to, single linkage, complete linkage, and average linkage.

In some embodiments, the properties of interest (Y values) may be non-numeric, such as when the property of interest is whether or not a molecule is active for some pharmaceutical purpose. In such cases, it may be necessary to represent the non-numeric properties of interest by a numeric value because clustering algorithms typically work on numeric data. One method to represent non-numeric properties is to "explode" each property for each item into a bit vector that has a length corresponding to the number of different "values" that the non-numeric property can have. For example, in the case of a property indicating whether or not a molecule is active, the bit vector would have one bit to represent that the molecule is active (1) or is not active (0). For classifications involving two or more properties, the bit in each vector that corresponds to each separate property "value" will be set to 1. The remaining bits will be set to 0. Since X values have different units and different size ranges, a scaling may be performed so that each value enters the clustering algorithm on a roughly equal footing. Since typically there are many more X values than Y, an additional scaling factor may be applied to all X values so that collectively, the Y values contribute roughly equally.

The usefulness of using tests and thresholds based on clusters is surprisingly insensitive to the number of clusters chosen. In one embodiment, twice as many clusters as there are properties of interest are defined.

In one embodiment, the clustering method follows this procedure:

1. Establish Y variables and X variables.
2. Explode non-numeric Y values into bit vectors.
3. (Optionally) reduce the number of X variables with PCA
4. Reduce the scale on the more numerous X variables so that all of the X's collectively contribute as much as the Y variable.
5. Perform the clustering to obtain a specified number of clusters.

In some embodiments, clustering is used only during tree growth. Thus, only training items would be clustered. Clustering would not be used when predicting the properties of new items.

An additional way to generate tests or thresholds is to use a greedy-based score. A "greedy score" refers to selecting a test or threshold that will achieve the greatest improvement in prediction error rate irrespective of any subsequent nodes. Greedy score considers only the effect on the immediate children of the split. Thus, a greedy-based test or threshold is based on improvement in prediction error rate based on the properties of interest. Items classified by a greedy-based score are not further classified. That is, the branches coming from a greedy-based test or threshold always end in a leaf node. Because eventually a training set is exhausted of items, there must be a final partitioning step to any recursive partitioning algorithm. As a practical matter, when to make a final partition is a matter of user preference and is generally dictated by a balance of the simplicity of the tree against the desired accuracy and completeness of the tree. Upon deciding that it is appropriate to make a final split, a preferred method for making this split is to use a greedy score. Greedy score is therefore considered the best way to end a recursive partitioning algorithm because it achieves a prediction accuracy that is as good as or better than any other single test or threshold.

Although greedy score can be used at any level to make the best one-step improvement in prediction accuracy, greedy score is generally not preferred at levels other than the last level because a greedy score test could foreclose a highly beneficial test in an additional node lower in the hierarchy. However, in some embodiments, a greedy-based test or threshold is included as one of the alternative tests or thresholds in a super tree.

Figure 4:
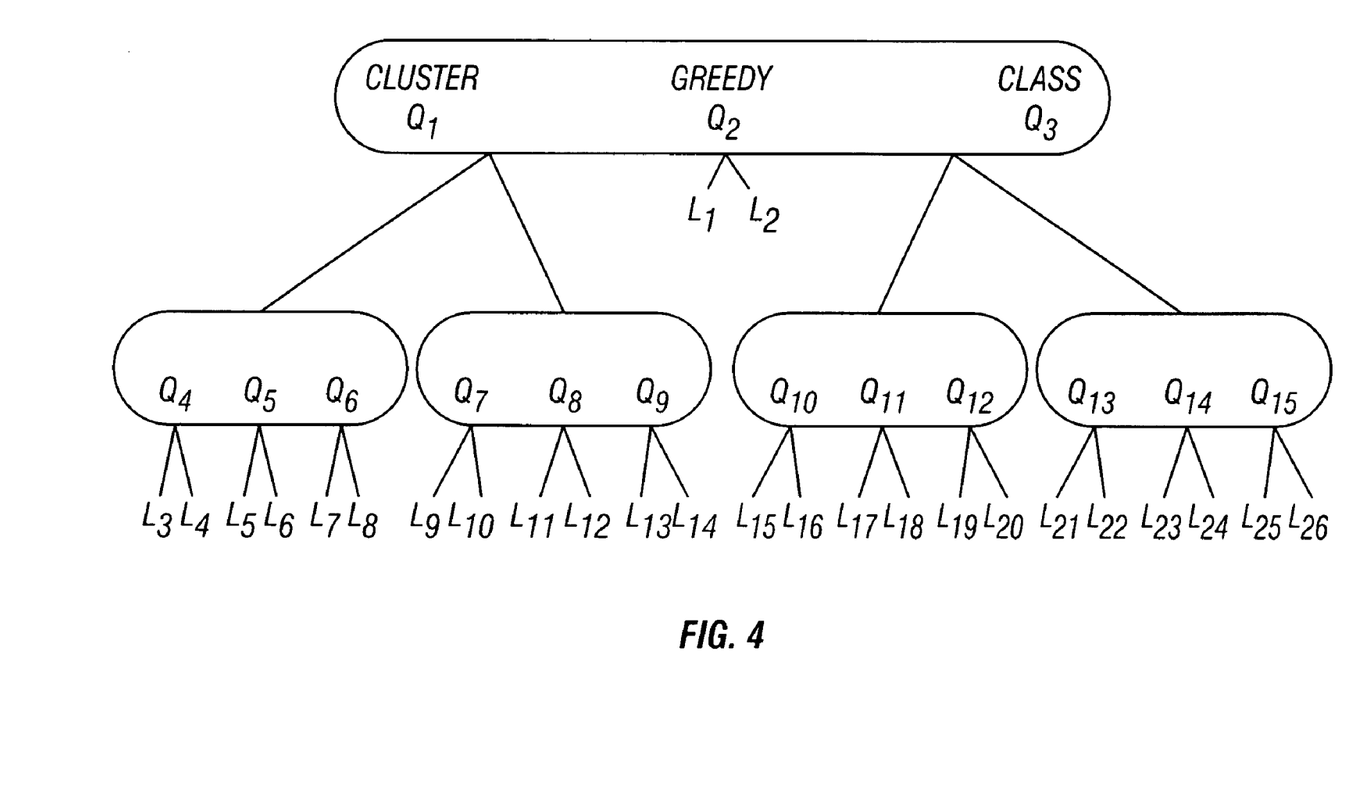
FIG. 4 illustrates a super tree using cluster-based, class-based, and greedy score alternative tests.

In one embodiment, illustrated in FIG. 4, a super tree is grown wherein each node comprises a class-based test or threshold, a cluster-based test or threshold, and a greedy-based test or threshold. The branches from each class-based and cluster-based test or threshold are continued in depth such that they lead to additional nodes containing the three alternative tests or thresholds. The branches from the greedy-based test or threshold are not continued in depth and instead, lead to leaf nodes. In other embodiments, multiple class-based and cluster-based tests or thresholds can be included as alternatives in each node.

Pruning a Super Tree

A number of pruning approaches may be employed to prune a tree. One approach is called minimal cost-complexity pruning. The tree pruning process starts at a leaf node and prunes away branches until a sub-tree of the original tree is left. Since multiple sub-trees may be formed from a tree by a pruning process, minimal cost complexity pruning selects a sub-tree that minimizes the function $R_\alpha = R_0 + \alpha N_{leaf}$, where $R_0$ is the miscalculation cost on the training data set, $N_{leaf}$ is the number of leaf nodes, and $\alpha$ is a complexity parameter that controls the size of the tree. Therefore, $R_\alpha$ is a combination of the miscalculation cost of the tree and its complexity. In general, miscalculation cost is the cost or loss of misclassifying an item as having one property value, when the item in fact has a different property value. For a formal definition of miscalculation cost, please refer to pp. 35-36 of CART. Using minimal cost complexity pruning, the pruning process successively cuts off branches until the function $R_\alpha = R_0 + \alpha N_{leaf}$ stops decreasing. Multiple values of $\alpha$ can be used to produce varying sub-trees. In one embodiment, values of α are found by bracketing and bisection. α is bracketed by a user-defined minimum value and a maximum value equal to 0.5 times the error rate at the root of the tree. Bisection of a is conducted such that the smallest difference in different values of α is the minimum error cost and the smallest difference in sub-trees found is one leaf. In one embodiment, all values of α that produce a unique tree are found. For a more detailed description of the pruning process, please refer to pp. 63-81 of CART.

Besides removing branches, pruning a super-tree also involves discarding all but one alternative test or threshold at each node. It is generally desirable to prune the super-tree repeatedly to find all of the unique solutions and ultimately evaluate these to determine the best solution or solutions.

Figure 5:
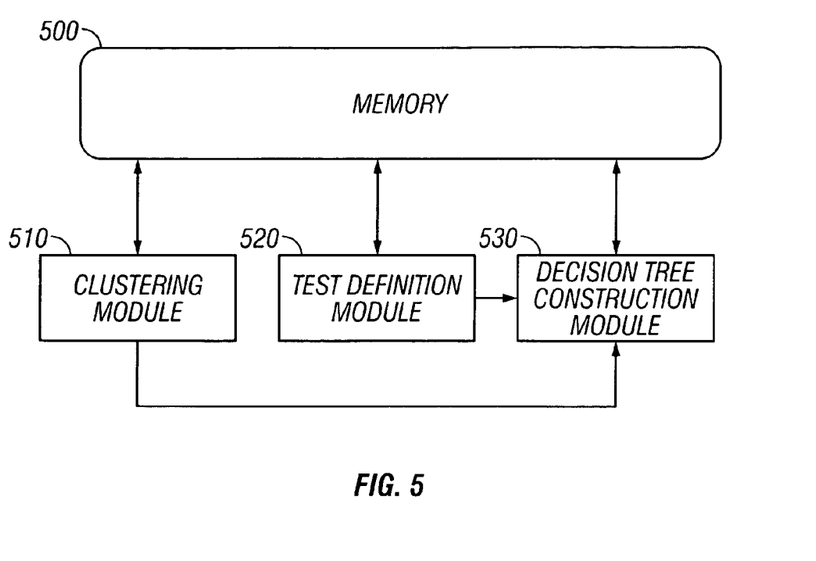
FIG. 5 illustrates a computer-implemented system for creating a decision tree.

In one embodiment, illustrated in FIG. 5, a computer-implemented system is provided for constructing decision trees using chart-ahead recursive partitioning. As will be understood by those of skill in the art, the methods described herein can be implemented on general purpose computer systems with well known components such as processing circuitry, memory, input devices, displays, etc.

In this embodiment, a memory 500 is provided for storing the descriptors for a set of training items. Behavioral classifications defining the items' physical behavior with respect to a property or attribute of interest is also stored in memory 500 for each item. A clustering module 510 is attached to the memory 500. The clustering module 510 assigns each of the training items stored in memory 500 into one of a number clusters based on similarities in characteristics and behavioral classifications. A test definition of module 520 is attached to both the memory 500 and the clustering module 510. The test definition module defines tests or thresholds based on one or more of the training items' characteristics for separating the training items into separate groups. A decision tree construction module 530 is attached to the memory 500, clustering module 510, and test definition module 520. The decision tree construction module 530 stores a hierarchical set of nodes, where each node is defined by a test or threshold created by the test definition module 520. The decision tree construction module 530 can store several alternative node definitions for each node. One of the alternative node definitions produces a maximum association between the separate groups produced the node's test or threshold and the clusters defined by the clustering module 510. Another of the alternative node definitions produces a maximum association between the separate groups produced the node's test or threshold and the behavioral classifications of the set of training items. In one embodiment, the decision tree construction module 530 contains an alternative node definition selection module that selects among possible alternative node definitions for each of a series of nodes based on the predictive accuracy of the series of nodes in separating training items based on their behavioral classifications.

EXAMPLE 1

Solving the Exclusive-OR Problem Using Chart-Ahead Partitioning

Figure 6:
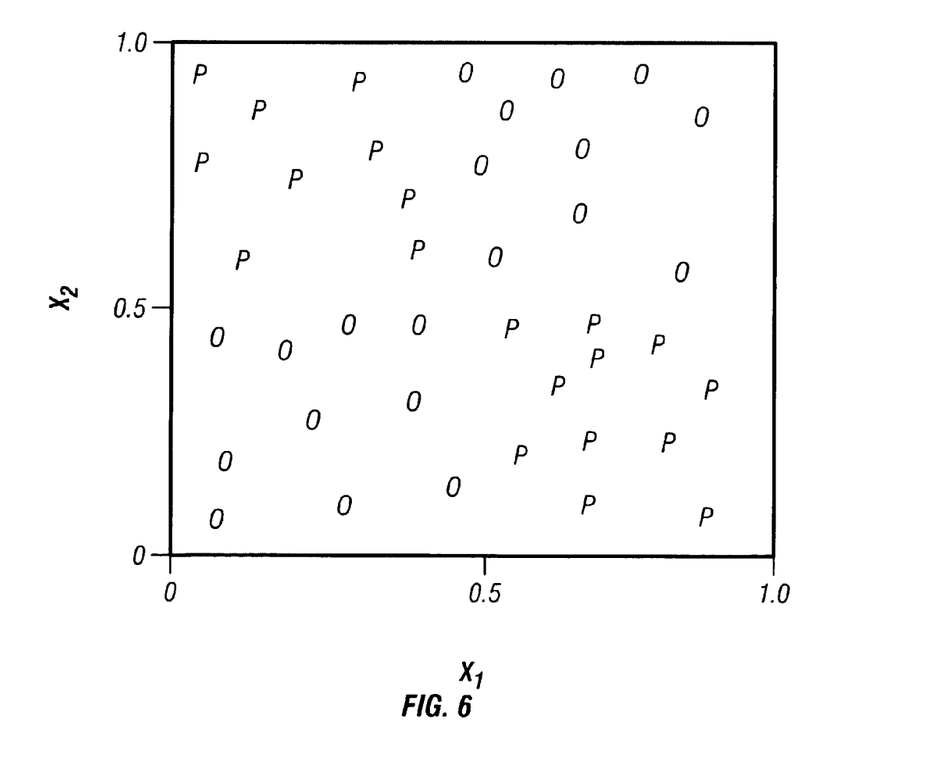
FIG. 6 illustrates an exclusive or problem.

FIG. 6 depicts an exclusive-or (XOR) problem, which is a known type of classification problem that conventional recursive partitioning is unable to handle effectively. A set of items is depicted on a grid. Each item has an $X_1$ value (its numeric value along the $X_1$ axis), an $X_2$ value (its value along the $X_2$ axis), and a Y value indicating whether the item exhibits a particular property (P) or does not exhibit the particular property (0). In this example, items exhibit the property if either $X_1$ or $X_2$ is greater than 0.5 but not if both $X_1$ and $X_2$ are greater than 0.5. This is known as the exclusive-or problem.

A decision tree would consist of a series of nodes that perform tests based on items $X_1$ and $X_2$ values with the goal that it would accurately predict whether an item has the property or does not. Although the solution is readily apparent to the eye, conventional recursive partitioning is unable to generate a decision tree that solves the problem. Indeed, conventional recursive partitioning can't even make the first step; it breaks down because there is no test or threshold based on either $X_1$ or $X_2$ values that increases class purity (any resulting classes would still be a roughly equivalent mix of items with and without the property).

In contrast, a solution can be found using a chart-ahead approach as described herein. Two hundred training items were provided with various $X_1$ and $X_2$ values. A Hierarchical Ward clustering algorithm was applied to the training items yielding four clusters (one in each quadrant of FIG. 6). A super tree was created that included alternative tests based on the best cluster-based score and best class-based score in each node. After appropriate pruning, the best decision tree was produced. The decision tree consisted of a test of $X_2 \leq 0.49345$ for the first node and tests of $X_1 \leq 0.4959$ for the two nodes at the second level of the hierarchy. The result was that only four errors in classification prediction occurred in the training set with the tree constructed. Using the methods described herein, an appropriate test for the first node was found by choosing the test producing the best cluster-based purity increase, which is the test that most accurately classifies the items into categories or groups containing the fewest different clusters after partitioning. In this case, the first partition produced two groups of two clusters each from the original set of items that included four clusters.

EXAMPLE 2

MAO Inhibitor Set

Chart-ahead partitioning was applied to a set of MAO inhibitor molecules with the goal of creating a decision tree for predicting a molecule's activity for MAO inhibition. 1641 molecules were provided in the training set. The property of interest was activity, which classified into four distinct classes (Y values): inactive, low-active, medium-active, and high-active. Each molecule was also characterized by 87 numeric X descriptors. The set of molecules were clustered by a clustering algorithm into 8 clusters. Alternative tests considered for nodes in the super tree included the two best class-based scores and the two best cluster-based scores. The maximum depth of the produced super tree was 8 with a maximum depth of 5 for considering alternative branches. Prediction errors were weighted by class frequency.

Prediction errors for various sized decision trees (sub-trees after pruning) are shown in Table 1 with a comparison between using conventional recursive partitioning and chart-ahead recursive partitioning. It was observed that chart-ahead partitioning consistently produced lower errors than conventional partitioning for the same size tree.

TABLE 1

Errors using MAO inhibitor training set.

| Number of Leaves | Conventional Error | Chart-ahead Error |
|---|---|---|
| 19 | 693 | 591 |
| 9 | 807 | 741 |
| 3 | 942 | 936 |
| 2 | 1065 | 1047 |

EXAMPLE 3

Proprietary Assay

A training set consisting of 33140 molecules was used. The property of interest (Y value) was whether or not the molecules were active. In the training set, 33031 molecules were inactive and 109 were active. Each molecule was also characterized by 199 numeric X descriptors. A clustering algorithm was applied to divide the molecules into four clusters. Alternative tests included the 2 best class-based scores and the 2 best cluster-based scores. The maximum depth of the produced tree was 10 with a maximum depth of 5 for considering alternative branches. Prediction errors were weighted by class frequency.

Results comparing conventional and chart-ahead partitioning are shown in Table 2. Once again, it was observed that for the same size tree, chart-ahead partitioning yielded significantly lower error rates than conventional partitioning.

TABLE 2

Errors using proprietary assay training set.

| Number of Leaves | Conventional Error | Chart-ahead Error |
|---|---|---|
| 28 | 10342 | 6122 |
| 27 | 10345 | 6239 |
| 26 | 10349 | 6359 |
| 23 | 10364 | 6746 |
| 22 | 10373 | 6881 |
| 19 | 10428 | 7335 |
| 11 | 10608 | 8610 |
| 9 | 11020 | 8985 |

It has been discovered that trees created using the chart-ahead method are superior to those created using conventional recursive partitioning.

Chart-ahead construction allows optimization over a very large number of possible trees obtainable by following alternative splits in the super-tree. One best tree is obtained for each value of number of leaves. From these, the most effective tree or trees can be selected for further use.

It has also been discovered that the chart-ahead method is computationally feasible. Generally, only an extremely small fraction of the total number of possible trees is evaluated.

Further, the chart-ahead method of tree construction has been shown to be able to solve the XOR problem, chart-ahead-produced trees are never worse than those created by conventional recursive partitioning, and there is generally a 10% to 40% error reduction rate (for a given tree size) when using chart-ahead as opposed to conventional recursive partitioning.

The chart-ahead method can also be used to generate trees which can predict multiple Y properties which can include finding all unique trees for both $\alpha$ and $\beta$ values. For additional information regarding trees for multiple Y properties, see U.S. patent application Ser. No. 7,016,887, issued on Mar. 21, 2006, hereby expressly incorporated by reference in its entirety.

Also, the method of tree construction can be further refined by making a second run based on the results of the first run. Further, because multiple trees can be generated, those multiple trees can be used in predicting the unknown properties of new molecules. Multiple diverse trees will, in some cases, have predictive accuracy that surpasses that of single trees. The method is easily extended to regression trees (numeric Y properties) by using different scoring functions.

The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

What is claimed is:

1. A computer implemented method of forming a decision tree, said decision tree operating to provide predictions of at least one attribute of interest of a physical item, wherein the physical item has one or more measured or computed descriptors representative of one or more physical characteristics of the physical item, and wherein the physical item has one or more unknown attributes of interest which have not been physically measured or otherwise previously determined, the decision tree comprising two or more nodes in a hierarchical structure, wherein each node is defined by a test based on one or more of the physical items' descriptors, wherein the result of the test at a node operates to classify the physical item into one of two or more classes, and wherein the classification made at any given node determines the identity of a node lower in the hierarchy which is next applied to the physical item until a final node in the hierarchy is reached, and wherein the classification made by the final node comprises a prediction of the behavior of the physical item with respect to the unknown attribute of interest, the method of forming the decision tree comprising:

providing a set of training physical items, each training physical item in said set of training physical items having one or more measured or computed physical descriptors and one or more attributes of interest which have been physically measured or previously determined;

defining a set of two or more alternative tests for defining a selected node of the decision tree;

defining at least one test for defining at least one node lower in said hierarchy for each of said alternative tests previously defined for said selected node higher in the hierarchy;

applying said two or more alternative tests associated with said selected node to at least some of said set of training physical items;

applying said at least one test associated with said at least one node lower in said hierarchy to at least some of said set of physical training items;

determining the results of said applying;

choosing one of said alternative tests from said set based at least in part on said determined results;

defining said selected node by said chosen alternative test; and defining additional nodes to produce a completed decision tree containing said selected node.

2. The method of claim 1 wherein said one of said alternative tests is chosen by choosing as said one of said alternative tests a test that yields highest accuracy in predicting the one or more attributes of interest of the set of training physical items.

3. The method of claim 1 further comprising the step of dividing the set of training items into clusters having similar descriptor values and attributes of interest and wherein one of said two or more alternative tests is defined based on an improvement in cluster purity when said set of training items are classified by said test.

4. The method of claim 1 wherein one of said two or more alternative tests is defined based on an improvement in class purity when said set of training items are classified by said test.

5. A computer implemented method of forming a super tree, said super tree representing a plurality of decision trees, each decision tree operating to provide prediction of at least one property of interest of a physical item, wherein the physical item has one or more measured or computed descriptors representative of one or more physical characteristics of the physical item and one or more physical properties of interest, and wherein said super tree comprises a plurality of nodes in a hierarchical structure, said plurality of nodes defined by at least one test based on at least one of said one or more physical characteristics, wherein at least one of said plurality of nodes comprising a plurality of alternative tests such that each alternative test results in an alternative decision tree, the method comprising:

providing a set of training physical items, the set of items having one or more physical descriptors and one or more physical properties of interest;

creating a first node comprising two or more alternative tests based on one or more of the set of items' physical descriptors, wherein each test operates to classify training items into two or more first classes; and creating one or more additional nodes that comprise two or more alternative tests based on one or more of the set of items' physical descriptors, wherein each alternative test in each additional node classifies the training items from at least one of said first classes into two or more second classes.

6. A computer implemented method of clustering a set of items, the set of items having a plurality of numeric physical descriptors and one or more physical properties, at least one of the properties being characterized by a non-numeric value, the method comprising:

for each item, representing each property that has a non-numeric value with a numeric value, wherein the step of representing comprises:

creating a bit vector for a set of properties having a non-numeric value, wherein each bit of said vector corresponds to a property having a non-numeric value, wherein each bit vector comprises one bit for each distinct non-numeric property that each item can have, and setting the bit to a designated value if the bit corresponds to a non-numeric property that the item to which the bit vector corresponds has, and selling the bit to a different designated value if the bit corresponds to a non-numeric property that the item to which the bit vector corresponds does not have;

using a clustering algorithm to cluster the items into subsets of items; wherein each item within a subset has similar numeric physical descriptor values, wherein each item within a subset has similar values in said bit vector that represent non-numeric property values, and wherein each item within a subset has similar values for properties inherently characterized by a numerical value, if any.

* * * * *

UNITED STATES PATENT AND TRADEMARK OFFICE
CERTIFICATE OF CORRECTION

PATENT NO. : 7,269,597 B2 Page 1 of 1
APPLICATION NO. : 10/737722
DATED : September 11, 2007
INVENTOR(S) : Thomas P. Stockfisch It is certified that error appears in the above-identified patent and that said Letters Patent is hereby corrected as shown below:

Column 11, line 4, which reads "a", should read -- α --

Column 16, line 25, in claim 6, which reads "selling", should read -- setting --

Signed and Sealed this

Eighth Day of April, 2008

JON W. DUDAS
*Director of the United States Patent and Trademark Office*